United States Patent [19]

Larson et al.

[11] Patent Number: 5,229,604
[45] Date of Patent: Jul. 20, 1993

[54] SELF-FILLING AND SELF-PURGING APPARATUS FOR DETECTING SPONTANEOUS RADIATION FROM SUBSTANCES IN FLUIDS

[75] Inventors: I. Lauren Larson, Oak Ridge; Marion M. Chiles, Knoxville; V. Clint Miller, Concord, all of Tenn.

[73] Assignee: Martin Marietta Energy Systems, Inc., Oak Ridge, Tenn.

[21] Appl. No.: 825,749

[22] Filed: Jan. 27, 1992

Related U.S. Application Data

[63] Continuation of Ser. No. 524,254, May 15, 1990, abandoned.

[51] Int. Cl.⁵ .............................................. G01N 31/00
[52] U.S. Cl. ..................................... 250/255; 250/256; 250/364; 250/435
[58] Field of Search ............... 250/364, 435, 461.1, 250/461.2, 255, 256; 356/317, 318, 417

[56] References Cited

U.S. PATENT DOCUMENTS 4,464,338  8/1984  Dotson et al. ..................... 422/78

FOREIGN PATENT DOCUMENTS 1287232  4/1961  France ......................... 250/364
0123987  9/1979  Japan .......................... 250/364

*Primary Examiner*—Jack I. Berman
*Assistant Examiner*—Jim Beyer
*Attorney, Agent, or Firm*—George L. Craig; Harold W. Adams

[57] ABSTRACT

Disclosed herein is a radiation detector providing for the in situ automatic sampling of fluids containing substances emitting radiation, especially Cerenkov radiation. The detector permits sampling within well casings and is self-purging such that no additional provisions must be established for the storage and disposal of contaminated fluids.

10 Claims, 2 Drawing Sheets

SELF-FILLING AND SELF-PURGING APPARATUS FOR DETECTING SPONTANEOUS RADIATION FROM SUBSTANCES IN FLUIDS

This invention was made with Government support under contract DE-AC05-84OR21400 awarded by the U.S. Department of Energy to Martin Marietta Energy Systems Inc. and the Government has certain rights in this invention.

This application is a continuation of application No. 07/524,254, filed May 15, 1990, now abandoned.

BACKGROUND OF THE INVENTION

1. Field of Invention

This invention pertains to an apparatus and method for in situ detection of radiation. More particularly, the invention pertains to in situ detection of radiation in limited access areas such as well-logging bore holes.

2. Description of Prior Art

The importance of rapid, precise, real-time measurement and surveillance of radiation-emitting substances such as radionuclides that have the potential for severe adverse effects on public health cannot be overemphasized. Where it is known that such substances exist in waste disposal sites or where it is suspected that the substances may have intruded into underground aquifers or public water supplies for example, it is imperative that continuous, real-time, precise tracking of the substances be obtained. Such surveillance and sampling should also permit remote and automated operation and should not further complicate the problem by the accumulation of large numbers of contaminated samples requiring proper storage and disposal and always at risk of potential mislabeling by field personnel. Additionally, the sample apparatus and procedure should not affect the environment being measured such that the reliability of the sample is assured.

Four principle types of electromagnetic radiation are generated by the radiation-emitting substances for which surveillance is desired. A first type is bremsstrahlung radiation which is produced by the deceleration or acceleration of charged particles such as when an electron is near the field of an atomic nucleus. Another type is fluorescence which occurs when a substance emits radiation of one frequency when exposed to radiation of another frequency. A third type of radiation occurs from the phenomena known as the Compton effect in which the wavelength of X-ray or gamma-ray photons is increased as a result of these photons striking an electron. Cerenkov radiation, the fourth type, is produced when charged particles pass through a transparent solid or liquid medium faster than the speed of light in the same medium. Of the four types, Compton effect radiation and fluorescence require the presence of external excitation radiation whereas bremsstrahlung and Cerenkov radiation result from the presence of charged particles, for example beta particles, inherent in the sample itself and have frequencies specific to the substance emitting the charged particle. Therefore the latter two types of radiation are much more easily adapted to in situ measurement of radiation in locations where access is restricted or difficult.

Two principle approaches have been followed in the monitoring and measurement of beta radiation in aqueous samples. Evaporation is the usual method for preparing aqueous samples for measurement of beta radiation. Major disadvantages exist, however, in that the samples must be taken to a laboratory for preparation and radiation losses occur from the adsorption on evaporation vessels and from the volatility of some compounds. Additionally, the samples may take weeks or months to process. Using bremsstrahlung radiation, the second approach, requires compilation of libraries of reference spectra of all background contributions from other radiation sources in order to detect the radionuclide emitting the beta particles. Such a library is specific to the many parameters of the location in which sampling is conducted. The present invention, on the other hand, uses the principle of Cerenkov radiation in a sampling device which avoids all the limitations of the abovementioned conventional approaches in that (1) there is no necessary sample preparation or transport; (2) no sample losses occur from evaporation or adsorption; (3) no reference library of spectra need be developed specific to the test site in order to ascertain the presence of a beta-emitting radionuclides; (4) the test site is not disturbed by the sample procedure; and (5) no provision must be made for the collection, storage and disposal of contaminated samples.

The in situ detector of the present invention permits in-place screening of fluid media for radiation emitting substances, especially radioactive contaminants, and sample analysis in real time. By way of example and not limitation, screening of radioactive energetic beta-/gamma ray contamination can be accomplished within approximately one-half hour of monitoring which is orders of magnitude faster than any presently available technology. The detector may also be permanently emplaced with remote-sensing capability and computer-controlled processing, which allows for rapid assessment of contaminant concentration and migration, data storage and retrieval and no necessity for exposure of person(s) to risks inherent at the sample site.

SUMMARY OF THE INVENTION

The principle object of invention is to provide an apparatus and method for in situ detection and measurement of radiation from substances emitting or scattering radiation in fluids.

A further object of invention is to provide an apparatus and method for remote real-time detection and measurement of radiation from fluids in hard to access locations such as well casings.

With these objects in view, the present invention is accomplished by a radiation detector comprising a cell for containing a fluid from which radiation is emitted, said cell having radiation-transparent faces and an inlet and outlet aperture; a sensor array adjacent said cell for generating a signal in response to said radiation transmitted through said faces; inlet and outlet tubes coupled respectively to said inlet and outlet apertures for transporting said fluid between a source of said fluid to be sampled and said cell; circuitry coupled to said sensor array to transmit said signal to a display; and a protective casing enclosing said cell, said sensor array and said circuitry.

The present invention is also accomplished by a method of testing a fluid for the presence of substances emitting radiation comprising the steps of introducing a fluid from a source into a cell enclosed by a protective casing, said cell having at least a pair of faces transparent to said radiation, said cell further having an inlet and an outlet aperture; transporting said fluid to be tested from said source to the interior of said cell; sensing said radiation transmitted through said faces of said cell by said substances emitting radiation in said fluid; generating a signal in response to said sensing of said radiation; and removing said fluid to be tested from said interior of said cell by returning said fluid to said source as said cell in said casing is withdrawn from said source.

DESCRIPTION OF THE OFFICIAL DRAWINGS

DESCRIPTION OF THE PREFERRED EMBODIMENT

Figure 1:
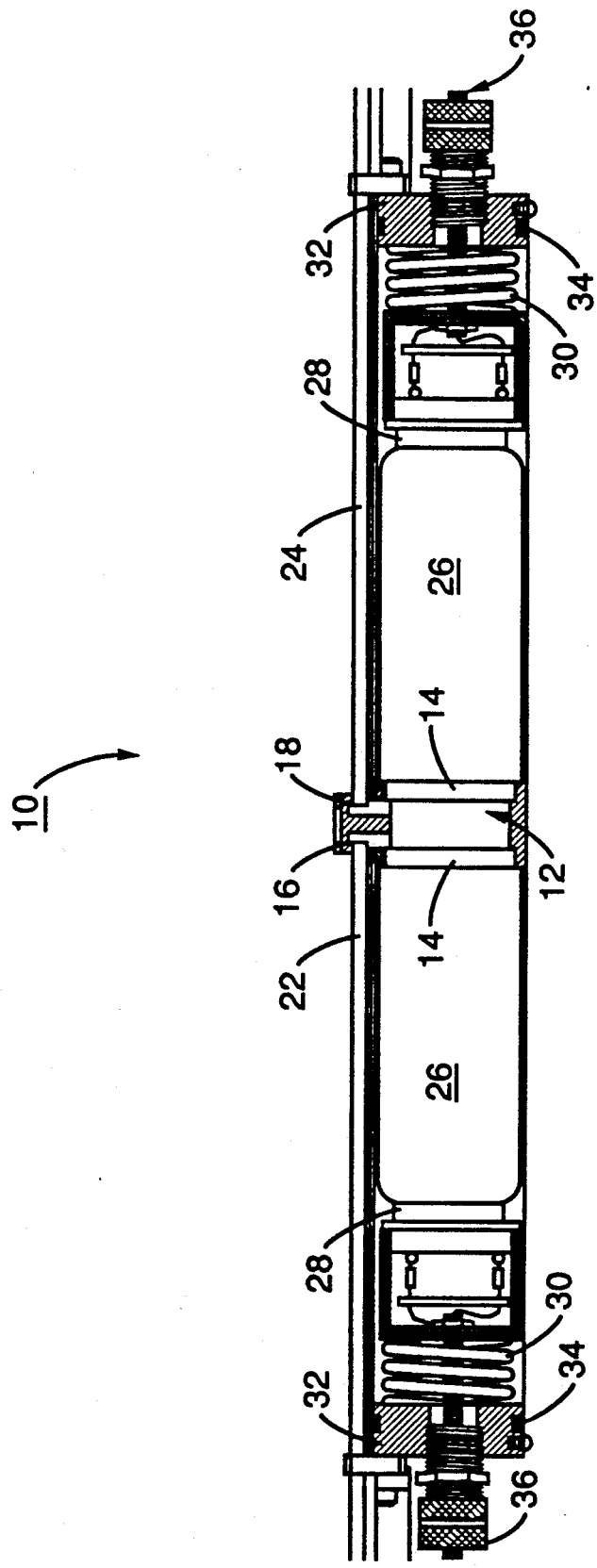
FIG. 1 is a schematic cross-section of a preferred embodiment of a detector made according to the invention.

Referring to FIG. 1, a schematic cross-section view is shown of a detector 10 made according to the present invention. A cell 12 having a pair of radiation transparent windows 14 and inlet and out apertures 16,18 is located inside a protective casing 20 forming the exterior surface of the detector 10. Inlet(fill) and outlet(vent) tubes 22,24 are attached to the casing 20 and respectively connected to the inlet and outlet apertures 16,18. Photodetectors 26, a pair of photomultiplier tubes for example, are then positioned inside the casing 20 adjacent the radiation transparent windows 14 of the cell 12 to sense radiation from substances in the fluid contained in the cell 12. In the example detector shown, each photomultiplier tube is held in place against an associated window 14 by a circular metal shield 28 and a compression spring 30. Each spring 30 is in turn held in place by an associated end cap 32 of the the protective casing 20. Intrusion of fluids into the interior of the casing 20 is prevented by incorporating a bushing 34, an o-ring for example, into the end cap 32. Electrical power for the photodetectors 26 is supplied by electrical leads 36, coaxial cable for example, routed through the end caps 32.

In operation, the detector 10 may be inserted into a fluid source, a groundwater well for example, and the fluid will enter the cell 12 via the inlet tube 22 and inlet aperture 16. Air trapped in the cell 12 is displaced by the fluid through outlet aperture 18 and outlet tube 24. Any radiation emitted by substances within the fluid is then sensed by the photodetectors 26 through the windows 14 of the cell 12 and a signal is transmitted from the photodetectors 26 via the electrical leads 36 to a remote display. The detector may then be withdrawn from the fluid source and, in the case of the groundwater example, the fluid within the cell 12 will drain from the cell through the outlet tube 24 and outlet aperture 18 under the pressure of the ambient atmospheric pressure. This self-purging feature is particularly advantageous in that numerous samples of the fluid source may be taken without disrupting the source or accumulating numerous samples that must be disposed of. Additionally, the open fluid path in the described embodiment permits a constant flow-through monitoring of a fluid where the detector is immersed in a fluid current.

Figure 2:
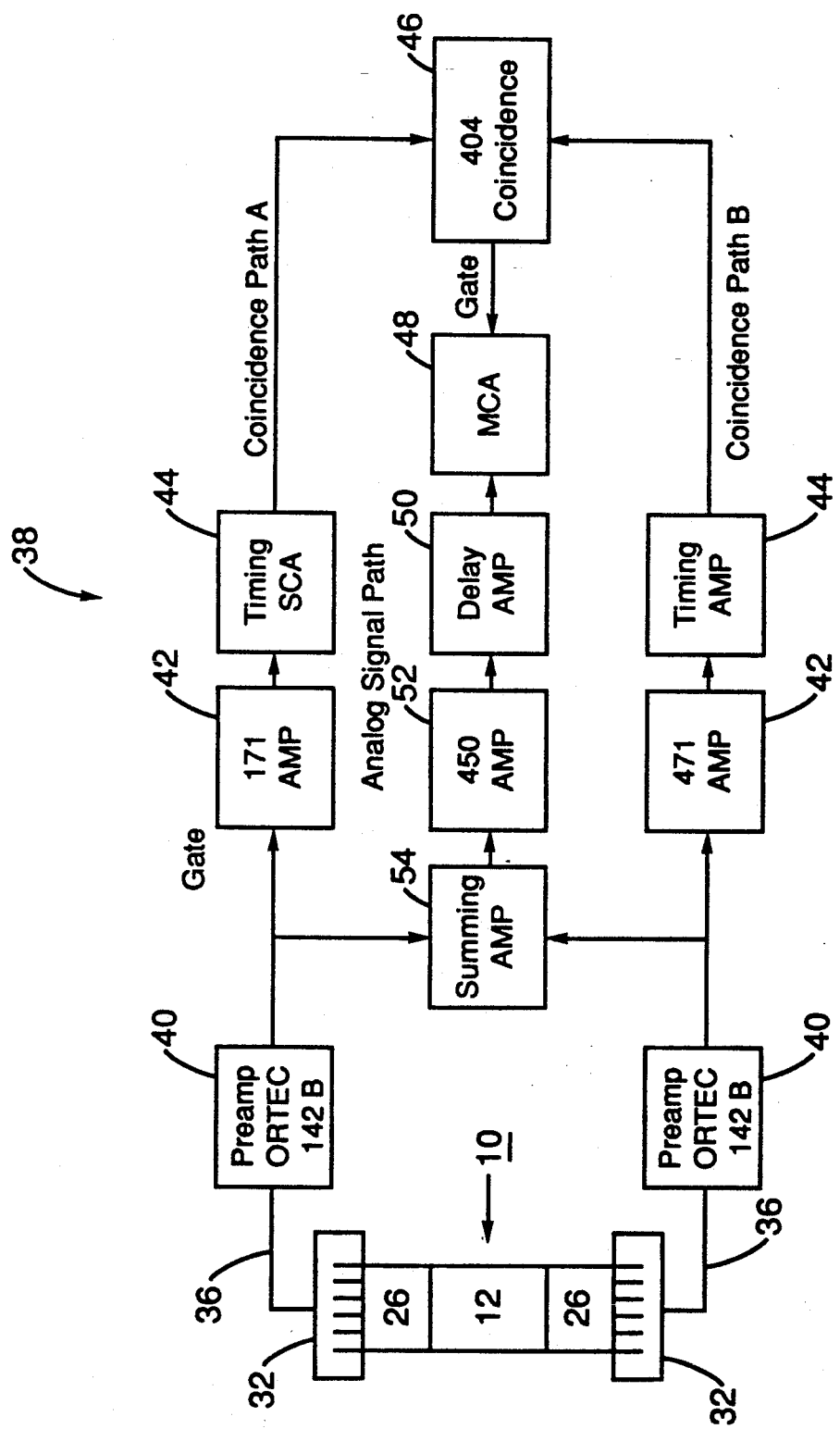
FIG. 2 is a block diagram of a coincidence circuit used in a preferred embodiment of the invention.

FIG. 2 illustrates a block diagram of an example coincidence circuit 38 used for each sampling cell 12 in the radiation detector of the present invention. Each coincidence circuit 38 has a signal coincidence path A and B with each path including a preamplifier 40 connected to receive a signal generated from an associated photodetector 26. Following the preamplifier in each path is a signal amplifier 42 connected to a timing single channel analyzer 44 which is in turn connected to a coincidence logic circuit 46. The coincidence logic circuit 46 transmits a gate signal from the two logic paths to a multi-channel analyzer 48 which is turned on by the gate pulse to receive a coincident analog signal. The analog signal is developed in the two coincidence paths A and B by the associated preamplifiers 40 and is also transmitted to summing amplifier 54 from each preamplifier 40. The summing amplifier 54 in turn transmits the analog signal to the analog amplifier 52 which then transmits the signal to delay amplifier 50. The signal is then transmitted from delay amplifier 50 to the multi-channel analyzer 48 to coincide with receipt of the gate pulse in the multi-channel analyzer and is stored according to its pulse amplitude.

The coincidence counting circuit 38 ensures that a signal has to occur in each photodetector 26 associated with a particular cell 12 before it is counted as a scintillation. By this means, noise pulses that may occur individually in each photodetector are rejected.

By way of example and not limitation, an embodiment of the described detector 10 has been designed for immersion in surveillance wells 7.6 cm in diameter and larger and is capable of detecting high energy beta particles such as those from strontium-90 and yttrium-90. For applications detecting only Cerenkov radiation, low energy beta particles are excluded because they do not give rise to Cerenkov radiation. Only high energy beta particles, i.e. $>0.263$ Mev, are detected as well as some gamma radiation. The coincidence circuit 38 further permits selection of a signal "window" to discriminate lower energy pulses from higher ones.

The description of the above invention is by way of example and not limitation and modifications to the described invention such as remote location of the photodetectors, providing pressure other than ambient atmosphere to move fluid into and out of the cell and the like are within the ambit of those skilled in the art. Such modifications are anticipated as being within the scope of the following claims.

We claim:

1. A detector of spontaneous radiation comprising:
   a) a cell for in situ immersion in a source of fluid having substances which emit said spontaneous radiation, said cell having at least first and second faces transparent to said radiation, said cell further having an inlet and an outlet aperture connected to its interior;
   b) inlet and outlet tubes for transporting said fluid between said source and said interior of said cell, said inlet and outlet tubes having internal ends respectively coupled to said inlet and outlet apertures and external ends exposed to ambient pressure such that said cell is self-filling and self-purging of said fluid;
   c) a sensor array adjacent said cell for generating continuous real-time signals in response to said radiation transmitted through said at least first and second faces;
   d) circuitry coupled to said sensor array to transmit said signals to a display; and
   e) a protective casing enclosing said cell, said sensor array and said circuitry.

2. The detector of claim 1 wherein said radiation is Cerenkov radiation.

3. The detector of claim 1 wherein said sensor array includes a pair of photodetectors.

4. The detector of claim 1 wherein said circuitry is a coincidence circuit receiving said signal from said sensor array, said coincidence circuit storing the amplitude of each pair of coincident signals.

5. The detector of claim 1 wherein said protective casing permits insertion of said detector in well casings.

6. A detector for sensing radiation spontaneously emitted by substances in a fluid comprising:
   a) a cell for in situ immersion in a source of said fluid, said cell having at least first and second portions transparent to said spontaneously emitted radiation, said cell further having an inlet and an outlet aperture connected to its interior;
   b) inlet and outlet tubes for transporting said fluid between said interior of said cell and said source of said fluid, said inlet and outlet tubes having internal ends respectively coupled to said inlet and outlet apertures and external ends exposed to ambient pressure such that said cell is self-filling and self-purging;
   c) a sensor array coupled to said cell for generating real-time signals responsive to said spontaneously emitted radiation transmitted from said interior of said cell through said portions;
   d) circuitry coupled to said sensor array to transmit said signals to a display; and
   e) a protective casing enclosing said cell.

7. The detector of claim 6 wherein said radiation is Cerenkov radiation.

8. The detector of claim 6 wherein said sensor array includes a pair of photodetectors optically coupled to said first and second portions of said cell.

9. The detector of claim 6 wherein said circuitry is a coincidence circuit receiving said signal from said sensor array, said coincidence circuit storing the amplitude of each pair of coincident signals.

10. A radiation detector for field surveillance of radiation in a groundwater well comprising:
   a) an elongate detector body having a cell interior to said body for receiving fluid from said well, said cell having at least a pair of opposed faces transparent to said radiation, said cell further having an inlet and an outlet aperture;
   b) a first photosensor interior to a first end of said body and adjacent one of said faces to sense said radiation spontaneously emitted in said fluid in said cell and transmitted through said face to said first photosensor;
   c) a second photosensor interior to a second end of said body opposite said first end and adjacent a second of said faces to sense said radiation spontaneously emitted in said fluid in said cell and transmitted through said second face to said second photosensor;
   d) an inlet and an outlet tube having respective internal ends respectively connected to said inlet and outlet apertures of said cell and respective external ends open to the ambient to respectively receive and discharge said fluid between said cell and said source of said fluid; and
   e) circuitry coupled between said first and said second photosensor and a display, said circuitry receiving first and second signals generated by respective said first and second photosensors in response to sensing said spontaneously emitted radiation and transmitting a third signal to a display.

* * * * *